US010631947B2

(12) United States Patent
Hasani bidgoli et al.

(10) Patent No.: US 10,631,947 B2
(45) Date of Patent: Apr. 28, 2020

(54) DEVICE FOR BRAIN BIOPSY

(71) Applicants: Javad Hasani bidgoli, Tehran (IR); Amirhossein Ahmadian, Tehran (IR); Mohammad Jalal Sadeghi, Tehran (IR); Alireza Ahmadian, Tehran (IR); Farzam Farahmand, Tehran (IR); Saeed Sarkar, Tehran (IR)

(72) Inventors: Javad Hasani bidgoli, Tehran (IR); Amirhossein Ahmadian, Tehran (IR); Mohammad Jalal Sadeghi, Tehran (IR); Alireza Ahmadian, Tehran (IR); Farzam Farahmand, Tehran (IR); Saeed Sarkar, Tehran (IR)

(73) Assignee: Paresh Intelligent Surgical System, Tehran (IR)

( * ) Notice: Subject to any disclaimer, the term of this patent is extended or adjusted under 35 U.S.C. 154(b) by 170 days.

(21) Appl. No.: 15/854,442

(22) Filed: Dec. 26, 2017

(65) Prior Publication Data

US 2018/0132962 A1 May 17, 2018

Related U.S. Application Data

(60) Provisional application No. 62/439,001, filed on Dec. 24, 2016.

(51) Int. Cl.
*A61B 90/11* (2016.01)
*A61B 17/00* (2006.01)
(Continued)

(52) U.S. Cl.
CPC ............ *A61B 90/11* (2016.02); *A61B 10/0233* (2013.01); *A61B 2017/00407* (2013.01);
(Continued)

(58) Field of Classification Search
CPC ................ A61B 17/3421; A61B 90/11; A61B 2017/3407; A61B 2090/103; A61B 17/00;
(Continued)

(56) References Cited

U.S. PATENT DOCUMENTS 5,597,146 A 1/1997 Putman
8,944,064 B2 2/2015 Akram et al.
(Continued)

FOREIGN PATENT DOCUMENTS

CN 104546066 A 4/2015
CN 103919591 B 4/2016

OTHER PUBLICATIONS

Kyoji Tsuda, Navigation-guided Endoscopic Biopsy for Intraparenchymal Brain Tumor, Journal of Neurol Med Chir, Jun. 2011, vol. 51, 694-700.
(Continued)

*Primary Examiner* — George J Ulsh
(74) *Attorney, Agent, or Firm* — Bajwa IP Law Firm; Haris Zaheer Bajwa

(57) ABSTRACT

Various devices and methods for guiding a biopsy surgical tool are disclosed. One type of surgical device includes a first rotational mechanism, a translational mechanism, and a second rotational mechanism. In some cases, the second rotational mechanism includes a circular frame and an end-effector. The yaw movement of the end-effector is effectuated via the first rotational mechanism. In addition, roll and pitch movements of the end-effector are effectuated via the second rotational mechanism. Furthermore, translational movement of the end-effector is effectuated via the translational mechanism.

11 Claims, 5 Drawing Sheets

(51) Int. Cl.
  *A61B 10/02* (2006.01)
  *A61B 90/00* (2016.01)
(52) U.S. Cl.
  CPC ............... *A61B 2017/00477* (2013.01); *A61B 2017/00725* (2013.01); *A61B 2090/035* (2016.02)
(58) Field of Classification Search
  CPC ............ A61B 34/20; A61B 2034/2055; A61N 1/0529
  USPC .......................................... 606/130; 600/427
  See application file for complete search history.

(56) References Cited

U.S. PATENT DOCUMENTS

| | | |
|---|---|---|
| 9,125,976 B2 | 9/2015 | Uber, III et al. |
| 2010/0042102 A1 | 2/2010 | Hamel |
| 2014/0371711 A1 | 12/2014 | Singh et al. |
| 2015/0119902 A1 | 4/2015 | Rurling et al. |
| 2016/0100895 A1* | 4/2016 | Piferi ................. A61B 17/3421 606/130 |
| 2016/0166324 A1 | 6/2016 | Nyman et al. |
| 2016/0193009 A1 | 7/2016 | Gowda et al. |
| 2016/0206383 A1* | 7/2016 | Leong .................... A61B 34/20 |

OTHER PUBLICATIONS

Saeid Abrishamkar, A New System for Neuronavigation and Stereotactic Biopsy Pantograph Stereotactic Localization and Guidance System, Journal of Surgical Technique and Case Report, Jul. 2011, vol. 2, Issue 3, 87-90.

* cited by examiner

DEVICE FOR BRAIN BIOPSY

CROSS-REFERENCE TO RELATED APPLICATION

This application claims the benefit of priority from U.S. Provisional Patent Application Ser. No. 62/439,001, filed on Dec. 24, 2016, and entitled "ACURECT FOR BIOPSY PROCEDURES" which is incorporated herein by reference in its entirety.

SPONSORSHIP STATEMENT

This application has been sponsored by Iran Patent Center, which does not have any rights in this application.

TECHNICAL FIELD

The present disclosure generally relates to biopsy systems and particularly to devices and methods that are used in frameless image-guided biopsy systems.

BACKGROUND

Brain surgeries are becoming an increasingly acceptable therapeutic and diagnostic modality in the neurosurgical treatment of patients suffering from chronic pain, Parkinson's disease, seizure, and other medical conditions. Among brain surgeries, brain biopsy is a common diagnostic surgery. A brain biopsy is the removal of a small piece of a brain tissue for the diagnosis of the brain abnormalities. A brain biopsy is generally used to diagnose Alzheimer's disease, tumors, infections, inflammations, and other brain disorders. By examining the tissue sample under a microscope, the biopsy sample provides the doctors with the information necessary for diagnosis and treatment. Generally, biopsy surgeries are categorized based on the technique and the needle size used for tissue extraction. A stereotactic biopsy, otherwise known as a core biopsy, is one of the least invasive types of biopsies. In a stereotactic biopsy procedure, 3-D imaging technology, as well as data from CT (Computer Tomography) and MRI (Magnetic Resonance Imaging) scans, are utilized to examine a sample from a tissue such as a brain tissue. Images that are taken in at least two planes may be used to pinpoint a tissue location (hereinafter referred to as a target), such as a tumor or microcalcifications in a breast. The pinpointed location may be used to help guide the tissue removal procedure. In a stereotactic biopsy procedure, the underlying principle of parallax may be utilized to determine the depth or "Z-dimension" of the target.

During different surgical procedures such as biopsies, and especially for stereotactic biopsies, some visual information may be simultaneously provided for the surgeon in real-time. One method that uses visual information includes detailed information of the 3D path the surgeon must pass in order to perform the biopsy, as well as the surgical instrument's tracking information. Facilitating the use of visual information and real-time tracking of instruments during the surgical procedures can help enhance the precision and quality of the surgeries.

In addition, stereotactic brain biopsy systems are also categorized based on the mechanism used to secure and position the biopsy device. A frame-based stereotactic biopsy system is considered the industry standard for evaluation of histological specimens from targets within the brain. For example, a frame-based stereotactic brain biopsy system requires attachment of a frame to the skull of a patient to assist the surgeon in locating and collecting a sample from a specific target within the brain. In this case the patient requires anesthesia during the procedure. Generally, the frame is attached to the patient by invasively inserting four screws into the skull. This frame-based method can provide the neurosurgeon with a generally safe and effective means for performing a biopsy retrieval.

However, the frame-based head fixation can be painful and the head movement limitation can be intolerable to many patients. Furthermore, there may be a risk of epidural hematoma, cranial fracture, and cerebrospinal fluid (CSF) leakage following the application of head pins, as well as lacerations of the scalp with patient movements, especially in young children. From the surgeon's perspective, rigid head fixation may also be problematic since the head pins are bulky and limit intraoperative flexibility as well as free movement of the surgical instrument. If the patient's head moves relative to a reference arc, the accuracy of the system is greatly reduced, potentially compromising successful execution of the procedure.

A frameless stereotactic biopsy procedure is a minimally invasive biopsy procedure, where the biopsy device is mounted on a Mayfield and the biopsy procedure performed under image guidance obtained from sectional imaging devices such as ultrasound/CT scan/MRI scan and other such imaging systems. Image guidance is required to select a least harmful path for the biopsy needle, so as to avoid vital organs and structures such as blood vessels or other sensitive regions. The needle may be positioned manually at an approximately correct angle/position by trial and error. In some cases this may be better carried out by using needle guiding devices that can guide the needle in the precise direction so as to reach the target point in the brain. The frameless stereotactic biopsies, generally, are integrated with an "end-effector" that is responsible for precisely guiding the needle.

However, in frameless brain biopsy procedures, fine positioning of the end-effector has been associated with challenges. For example, once the fine positioning of the end-effector is done, a locking mechanism is required to fix the end-effector at its position. Generally, fixing the end-effector of the frameless brain biopsy device is effectuated by tightening one or more screws. Tightening screws of the frameless brain biopsy device may displace the fine-positioned end-effector and consequently degrade the accuracy of the frameless brain biopsy procedure. In addition, the fixation of the frameless brain biopsy device screws is accomplished through a trial and error procedure that may substantially affect the cost, accuracy, and efficacy of the frameless brain biopsy procedure.

There is, therefore, a need in the art for frameless stereotactic biopsy systems and devices in which the fine positioning is accomplished more accurately and more easily without resorting to an inaccurate and time-consuming "trial and error" procedure.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In order to achieve more accurate and higher quality biopsies, a device may be utilized to provide a path for biopsy needle. Utilizing the disclosed device in a biopsy procedure may allow the surgeon to guide the biopsy needle/instrument exactly to the target and also may provide certain cost and size advantages relative to other biopsy procedures.

In one general aspect, the present disclosure is directed to a surgical device for guiding a biopsy surgical tool. The surgical device includes a first rotational mechanism configured to provide a first rotational degree of freedom about a yaw axis to the surgical device. The first rotational mechanism includes a connector connected movably to a distal end of a coarse-tuning section in a configuration rotatable about a roll axis, the yaw axis, and a pitch axis, a base, fixedly attached to a distal end of the connector, a ring-type member movably connected to a distal end of the base in a configuration rotatable about a yaw axis, a plurality of restraining cylinders attached to the distal end of the base, the ring-type member disposed rotationally and slidably between the plurality of restraining cylinders in a configuration limiting motion of the ring-type member to a rotation about the yaw axis, a pipe-shaped section provided at a distal end of the ring-type member, and a first frictional gripper attached to the base with a first lock screw mounted on the first frictional gripper, the first frictional gripper configured to minimize movements of the ring-type member in response to the first lock screw being tightened on the first frictional gripper. The surgical device also includes a translational mechanism configured to provide a translational degree of freedom along the roll axis to the surgical device. The translational mechanism includes a main rod disposed slidably, from a proximal end thereof, along a distal end of the pipe-shaped section of the ring-type member in a configuration limiting the movements of the main rod to a translational movement along the roll axis, a c-type connector fitted securely, from a proximal end thereof, to a distal end of the main rod, a second frictional gripper provided at the distal end of the main rod and a second lock screw mounted on the second frictional gripper, the second frictional gripper configured to minimize movements of the main rod in response to the second lock screw being tightened on the second frictional gripper. The surgical device further includes a second rotational mechanism configured to provide both a second rotational degree of freedom about the pitch axis and a third rotational degree of freedom about the roll axis to the surgical device. The second rotational mechanism includes a circular frame disposed coaxially and movably inside the c-type connector in a configuration rotatable about a pitch axis, a slotted rod disposed movably inside the circular frame in a configuration rotatable about the roll axis, an end-effector mounted securely on the slotted rod in a configuration synchronously rotatable with the slotted rod about the roll axis, a first worm gear attached to the circular frame and a first worm screw attached to the c-type member, the first worm gear meshing with the first worm screw in a configuration that is responsive to the first worm screw being turned in either a clockwise direction or a counterclockwise direction, the circular frame thereby rotating about the pitch axis, and a third lock screw, mounted on the c-type member in a configuration wherein tightening the third lock screw promotes friction between the third lock screw and the circular frame, thereby minimizing movements of the circular frame.

In another general aspect, the present disclosure is directed to a surgical device for guiding a biopsy surgical tool. The surgical device includes a first rotational mechanism configured to provide a first rotational degree of freedom about a yaw axis to the surgical device. The first rotational mechanism includes a connector connected movably to a distal end of a coarse-tuning section in a configuration rotatable about a roll axis, the yaw axis, and a pitch axis, a base, fixedly attached to a distal end of the connector, and a ring-type member movably connected to a distal end of the base in a configuration rotatable about a yaw axis.

The above general aspect may include one or more of the following features. In one example, the surgical device also includes a plurality of restraining cylinders attached to the distal end of the base, the ring-type member disposed rotationally and slidably between the plurality of restraining cylinders in a configuration limiting motion of the ring-type member to a rotation about the yaw axis. In another example, the surgical device includes a pipe-shaped section provided at a distal end of the ring-type member. As another example, there may be a first frictional gripper attached to the base with a first lock screw mounted on the first frictional gripper, the first frictional gripper configured to minimize movements of the ring-type member in response to the first lock screw being tightened on the first frictional gripper. In some cases, there is a translational mechanism configured to provide a translational degree of freedom along the roll axis to the surgical device, the translational mechanism including a main rod disposed slidably, from a proximal end thereof, along a distal end of the pipe-shaped section of the ring-type member in a configuration such that the movement of the main rod is limited to a translational movement along the roll axis, and a c-type connector fitted securely, from a proximal end thereof, to a distal end of the main rod. In addition, the device can include a second frictional gripper provided at the distal end of the main rod and a second lock screw mounted on the second frictional gripper, the second frictional gripper configured to minimize movements of the main rod in response to the second lock screw being tightened on the second frictional gripper. In one implementation, there may be a second rotational mechanism configured to provide both a second rotational degree of freedom about the pitch axis and a third rotational degree of freedom about the roll axis to the surgical device. The second rotational mechanism can include a circular frame disposed coaxially and movably inside the c-type connector in a configuration rotatable about a pitch axis, a slotted rod disposed movably inside the circular frame in a configuration rotatable about the roll axis, and an end-effector mounted securely on the slotted rod in a configuration synchronously rotatable with the slotted rod about the roll axis. In some implementations, a first worm gear is attached to the circular frame and a first worm screw attached to the c-type member, the first worm gear meshing with the first worm screw in a configuration that is responsive to the first worm screw being turned in either a clockwise direction or a counterclockwise direction, the circular frame thereby rotating about the pitch axis. In other implementations, a second worm gear is attached to the slotted rod and a second worm screw attached to the circular frame, the second worm gear meshing with the second worm screw in a configuration that is responsive to the second worm screw being turned in either a clockwise direction or a counterclockwise direction, the end-effector thereby rotating about the roll axis. In one example, a third lock screw is mounted on the circular frame in a configuration wherein tightening the third lock screw promotes friction between the third lock screw and the slotted rod, thereby minimizing movements of the slotted rod. In some cases, a fourth lock screw may be mounted on the c-type member in a configuration wherein tightening the fourth lock screw promotes friction between the fourth lock screw and the circular frame, thereby minimizing movements of the circular frame. In one implementation, the ring-type member is graded on an upper surface thereof, thereby facilitating measurement of the surgical fine-tuning device disposition in the direction of the first rotational degree of freedom. In another implementation, the main rod is graded on an outer surface thereof, thereby facilitating measurement of the surgical fine-tuning device disposition in the direction of the translational degree of freedom.

In another general aspect, the present disclosure is directed to a method of guiding the position of a biopsy needle. The method includes adjusting a coarse-tuning section of a surgical device to bring a fine-tuning section of the surgical device in close proximity to a target, and adjusting a fine-tuning section of the surgical device, wherein the fine-tuning section includes a first rotational mechanism, a translational mechanism, a second rotational mechanism, and an end-effector. The adjustment of the fine-tuning section includes rotating the fine-tuning section along a roll axis by repeated extending and retracting of the translational mechanism, rotating the fine-tuning section along the roll axis, a yaw axis, and a pitch axis by adjusting a first rotational mechanism that is connected to the coarse-tuning section by a ball-bearing mechanism, and securing the first rotational mechanism into a substantially fixed position by tightening a first lock screw, thereby increasing friction between a first frictional gripper and a ring-type member of the first rotational mechanism.

The above general aspect may include one or more of the following features. In one example, the adjustment of the fine-tuning section further includes rotating a circular frame in a C-type connector, the circular frame being associated with the C-type connecter by a first connecting rod and a second connecting rod that are fitted in lateral holes of the circular frame, and rotating the end-effector about the pitch axis by rotating a first worm screw that is engaged to a first worm gear disposed on an outer surface of the second connecting rod. In another example, the adjustment of the fine-tuning section further includes securing the end effector into a substantially fixed position relative to the yaw axis by tightening a second lock screw, thereby increasing friction between the third-lock screw and the first connecting rod. In some implementations, the method includes rotating a slotted rod, the slotted rod being disposed such that the slotted rod extends through a bottom hole and a top hole of the circular frame, and one end of the slotted rod is secured to the end effector. In some cases, the method includes disposing a biopsy needle guide in a passage formed in the end-effector through a slot formed in the slotted rod. As another example, the adjustment of the fine-tuning section may further include rotating the end-effector about the roll axis by rotating a second worm screw that is engaged to a second worm gear disposed on an outer surface of the slotted rod Other systems, methods, features and advantages of the implementations will be, or will become, apparent to one of ordinary skill in the art upon examination of the following figures and detailed description. It is intended that all such additional systems, methods, features and advantages be included within this description and this summary, be within the scope of the implementations, and be protected by the following claims.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1:
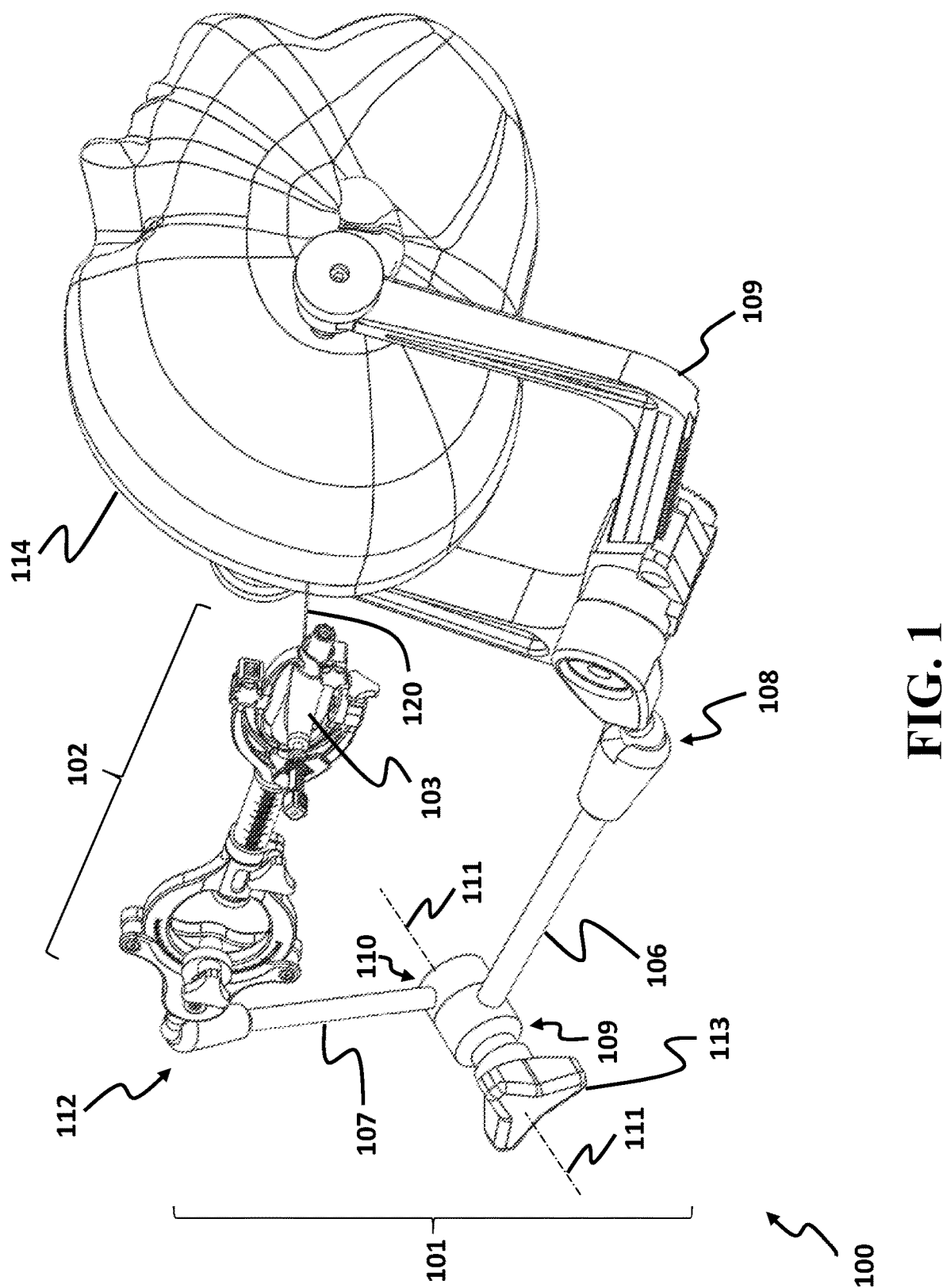
FIG. 1 illustrates an implementation of a surgical apparatus used to provide a path for a biopsy needle/instrument during a brain biopsy surgery.

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

The following disclosure describes techniques and systems for use of frameless stereotactic biopsy devices. The systems are designed to more readily provide the device with degrees of freedom in order to guide a biopsy needle to a target. As will be discussed below, such systems and methods can allow significant improvement and ease-of use in the operation of frameless stereotactic biopsy systems by offering the stable application of four degrees of freedom (DOFs).

In a frameless stereotactic biopsy system, visual information is provided by means of computer systems to a surgeon simultaneously (in real-time with the procedure) to allow the surgeon and/or medical team to analyze and control a patient's conditions. These computer systems and methods are referred to as "surgical navigation technologies". The use of a surgical device with surgical navigation technology may improve a surgeon's ability to use and rely on the visual information and real-time tracking of the instrument during a frameless stereotactic biopsy procedure. Furthermore, in some cases, the surgical device that is used in a stereotactic biopsy system may benefit from the capacity for independent motion and subsequent mounting positioning along four DOFs, which can be understood to simulate a human arm behavior. Such a feature allows a surgeon to have adequate control and maneuverability in securing the biopsy needle/instrument along the patient's skull through the surgical device.

In different implementations, the surgical devices that are used in biopsy surgeries are generally integrated with an end-effector which secures a path for the biopsy needle. For purposes of this disclosure, the term "end-effector" refers to a particular end linkage or segment that, depending on the design of the robot or machine, can securely grip, transport, orient, and release a workpiece/tool. In some implementations, the end-effector that may be used during brain biopsy surgery may generally include a sheath that may be provided with a passage for the biopsy needle. As described herein, the use of an integrated and exclusively designed surgical device, which provides a path for a biopsy needle/instrument, may enhance the precision and quality of the biopsy surgery. Furthermore, use of an integrated and exclusively designed surgical device may reduce the dependency of the biopsy surgery quality on the surgeon's dexterity.

In some implementations, the surgical apparatus of the present disclosure may include provisions for facilitating the positioning of the surgical device or portions thereof. For example, in some implementations, the surgical apparatus can include a "coarse-tuning" section and a "fine-tuning" section. In different implementations, the coarse-tuning section may be configured to allow the surgeon to position the end-effector of the surgical device in a space near or proximal to the target. Furthermore, in one implementation, the coarse tuning section may include a first rod and a second rod. In some implementations, a proximal end of the first rod, a proximal end of the second rod, a distal end of the first rod, and a distal end of the second rod may be equipped with rod end bearings such that the first rod and the second rod are able to be connected rotatably to another appliance (for example, another rod). A proximal end of the first rod may be mounted on a fixed rigid appliance that is present in a surgery room to allow the surgeon to rotate the first rod about the proximal end of the first rod, about three rotational axes (for example, a roll axis, a yaw axis, and a pitch axis). In some cases, in some implementations, the proximal end of the first rod may be mounted on a Mayfield surgical table or on a side rail of a surgical table, and/or a proximal end of the second rod may be mounted on a distal end of the first rod to allow the surgeon to rotate the second rod about the proximal end of the second rod, about a rotational axis, such as the yaw axis.

According to some implementations of the present disclosure, a proximal end of the fine-tuning section may be mounted on a distal end of the coarse-tuning section to allow the surgeon to rotate the fine-tuning section about the proximal end of the fine-tuning section, about three rotational axes (such as a roll direction, a yaw direction, and a pitch direction). As a result, the surgeon may position the fine-tuning section in a space near the target by rotating the first rod, the second rod, and then fine-tuning section about rotational DOFs of the coarse-tuning section. Furthermore, in some implementations, a locking mechanism may be used to lock the coarse-tuning section. For example, some screws may be provided in the structure to allow for locking/unlocking the coarse-tuning section. The surgeon may then loosen the screws to more generally position the fine-tuning section in a space near the target or otherwise, and/or the surgeon may tighten the screws to fix the fine-tuning section in position.

In some implementations, the fine-tuning section may be a device that is configured to provide one or more DOFs to the end-effector of the surgical apparatus. For example, in some implementations, the fine-tuning section of the surgical apparatus may include a translational degree of freedom and three rotational DOFs to allow for an accurate positioning of the surgical apparatus end-effector to the target. For purposes of reference, it should be understood that four DOFs are the minimum required DOFs to secure the end-effector of the surgical apparatus in this type of system. Thus, four DOFs are required in order to move a brain biopsy needle guide into an appropriate position and orientation for a biopsy procedure. However, in some implementations, the fine-tuning section of a surgical apparatus may include additional DOFs. In other words, in one implementation, the fine-tuning section of the surgical apparatus may allow for fine positioning of the end-effector of the surgical apparatus with respect to the target. In some implementations, one or more of the degrees of freedom of the fine-tuning section may be associated with a locking mechanism, such as, for example, a locking screw. The surgeon can thus loosen a locking screw to move the end-effector about the associated rotational degree of freedom, and/or the surgeon may tighten a screw to avoid movement of the end-effector in the direction of its associated degree of freedom. In some other implementations, in order to avoid positioning accuracy degradation as a result of tightening the lock screws, some set screws may be used for each degree of freedom in order to effectuate slight movement of the end-effector in the direction of the associated degree of freedom.

In order to provide greater clarity to the reader regarding the implementations disclosed herein, additional details are now provided with respect to the drawings. Referring to FIG. 1, one implementation of a surgical apparatus 100 that may be utilized to provide a path for a biopsy needle/instrument 120 in a frameless stereotactic brain biopsy system is depicted. The surgical apparatus 100 may include a coarse-tuning section 101 and a fine-tuning section 102. In one aspect, the coarse-tuning section 101 may be configured to allow the surgeon to position the fine-tuning section 102 of the surgical apparatus 100 in a space near the target. For example, in one implementation, the coarse-tuning section 101 may provide between four and seven DOFs to the surgical apparatus 100. Furthermore, in some implementations, the coarse-tuning section 101 may include more than seven DOFs to allow greater maneuverability as needed.

As shown in FIG. 1, in some implementations, the coarse-tuning section 101 may include a first rod 106 and a second rod 107. The first rod 106 may be mounted or otherwise attached from a proximal end 108 of the first rod 106 to a fixed rigid appliance that is present in a surgery room. Thus, the surgeon may be able to rotate the first rod 106 about the proximal end 108 of the first rod 106 about three rotational axes. For example, in one implementation, the first rod 106 may be mounted on a Mayfield 109. In alternative implementations, the first rod 106 may be mounted on a side rail of a surgical table (not shown in FIG. 1). In addition, in some implementations, the second rod 107 may be mounted from a proximal end 109 of the second rod 107 on a distal end 110 of the first rod 106 such that the surgeon may be able to rotate the second rod 107 about a first axis 111. In one implementation, the first axis 111 may be fixed on the first rod 106. Furthermore, in some implementations, the fine-tuning section 102 may be mounted or otherwise attached, from a proximal end of the fine-tuning section 102 to a distal end 112 of the second rod 107. Thus, the surgeon may be able to rotate the fine-tuning section 101 about the distal end 112 of the second rod 107 about three rotational axes (for example, a roll direction, a yaw direction, and a pitch direction). In some implementations, a lock screw 113 may be used to lock the DOFs of the coarse-tuning section 101 and thereby fix or secure the fine-tuning section 102 in position. Furthermore, the surgeon may loosen the lock screw 113 to move the coarse-tuning section 101 about the rotational DOFs of the coarse-tuning section 101 or tighten the lock screw 113 to prevent any externally-urged movement in the coarse-tuning section 101. In different implementations, other locking mechanisms may be used to prevent externally-urged movements of the coarse-tuning section 101. Utilizing the passive DOFs, the coarse-tuning section 101 may facilitate the positioning of the surgical apparatus 100 in a work-space of the biopsy surgery near a patient's head 114 by the surgeon.

In some implementations, the surgical apparatus 100 may be integrated with an end-effector 103. The end-effector 103 may be mounted or otherwise attached to a distal end of the fine-tuning section 102. In one implementation, the end-effector 103 may include a sheath 104 defining a passage 105 for the biopsy needle/instrument 120. In addition, in some implementations, the end-effector 103 may be configured to hold or store various biopsy needle guides. Benefits from this implementation may include but are not limited to increased accuracy of the biopsy surgery, for example by guiding the biopsy needle/instrument 120 through a biopsy needle guide that may securely guide the biopsy needle to the target.

Figure 2:
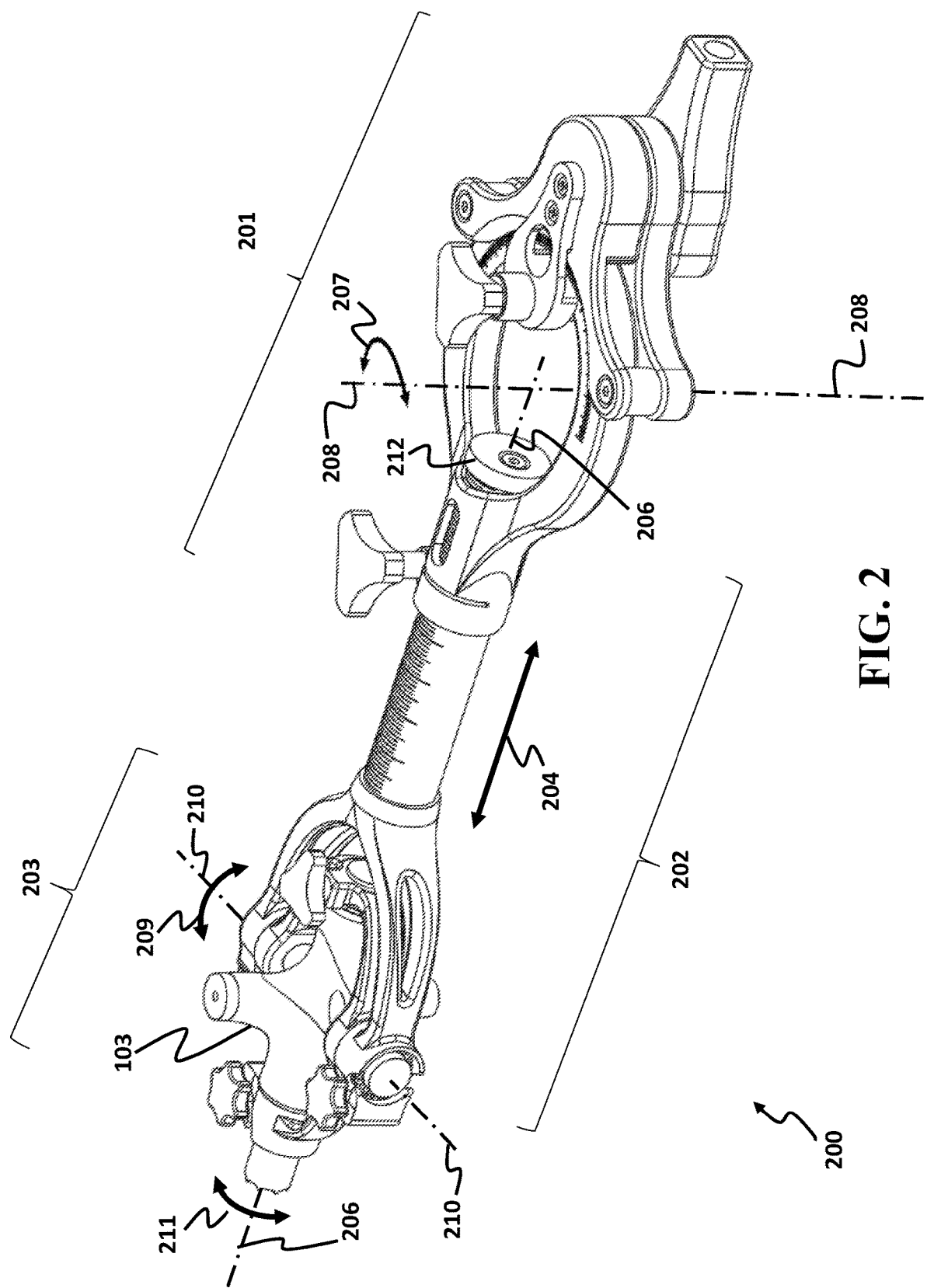
FIG. 2 illustrates a detailed perspective view of an implementation of a surgical device, which can be associated with various surgical apparatuses.

Referring now to FIG. 2, a surgical fine-tuning device 200 is depicted to illustrate one implementation of the fine-tuning section 102 of the surgical apparatus 100 of FIG. 1. The surgical fine-tuning device 200 may include a first rotational mechanism 201, a translational mechanism 202, a second rotational mechanism 203, and the end-effector 103. In some implementations, the surgical fine-tuning device 200 may include one translational degree of freedom 204 that allows for moving, for example, for extending and retracting the translational mechanism 202 along a roll axis 206 that may be a longitudinal axis of the translational mechanism 202. The surgical fine-tuning device 200 may further include three rotational DOFs: a first rotational degree of freedom 207 that allows for rotation of the translational mechanism 202 about a yaw axis 208, a second rotational degree of freedom 209 that allows for rotation of the end-effector 103 about a pitch axis 210, and a third rotational degree of freedom 211 that allows for rotation of the end-effector 103 about the roll axis 206. In other implementations, the surgical fine-tuning device 200 may have additional DOFs as desired.

Figure 3:
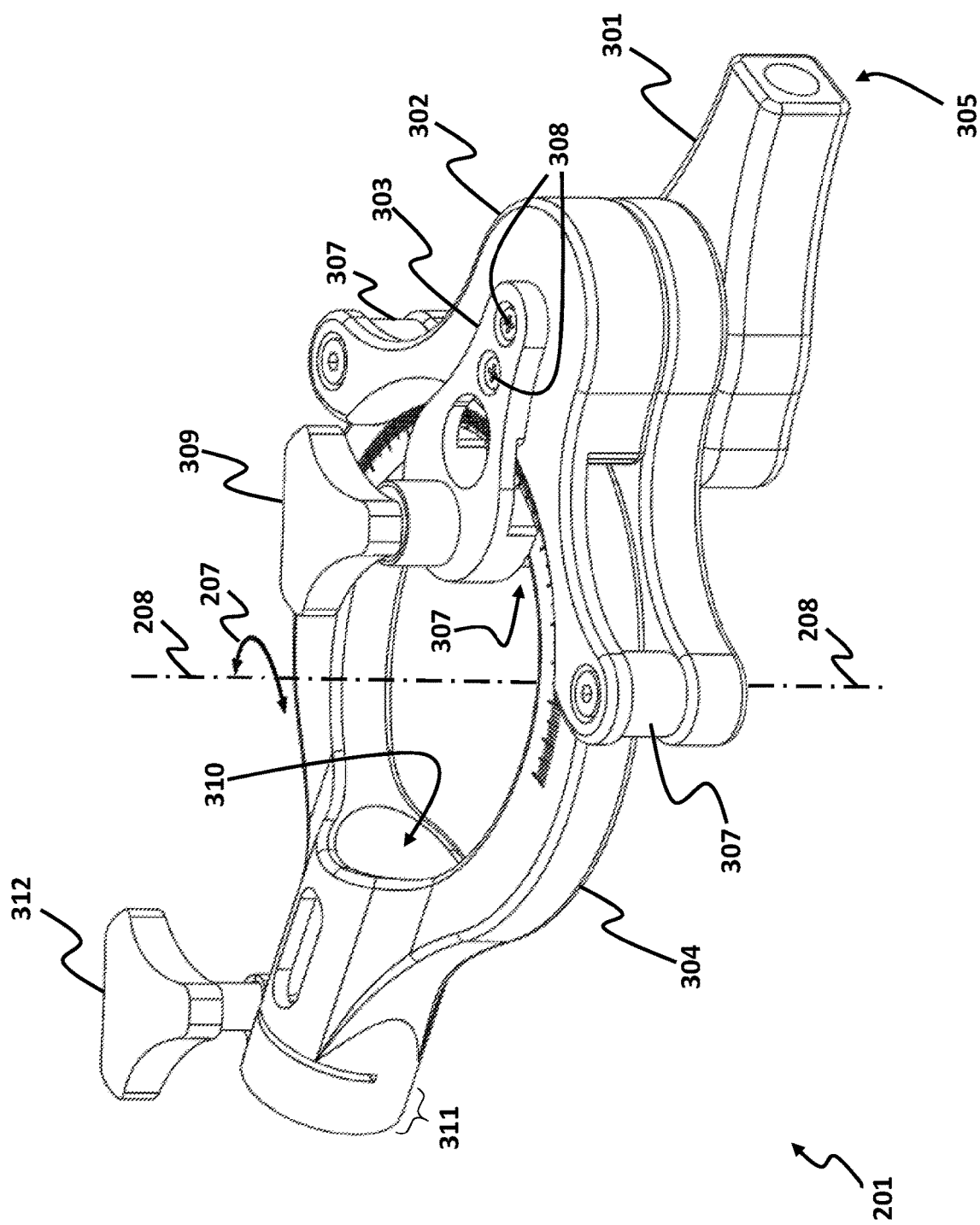
FIG. 3 illustrates a detailed perspective view of an implementation of a first rotational mechanism of a surgical device, which can be associated with various surgical apparatuses.

For purpose of reference, FIG. 3 provides an overview of various components and features for one implementation of the surgical fine-tuning device 200. The implementation of FIG. 3 is configured to provide at least the first rotational degree of freedom 207. With reference to FIGS. 2 and 3, in one implementation, the first rotational mechanism 201 may include a connector 301, a base 302, a first frictional gripper 303, and a ring-type member 304. The connector 301 may be connected from a proximal end 305 of the connector 301 to the distal end of the second rod (labeled 107 in FIG. 1) such that the surgeon is able to rotate the surgical fine-tuning device 200 about the distal end of the second rod (labeled 107 in FIG. 1) in three roll/yaw/pitch directions. For example, the connector 301 may be connected to the second rod (labeled 107 in FIG. 1) through a ball-bearing mechanism and/or any other similar connecting mechanisms. In some implementations, the base 302 may be mounted or otherwise be attached to a distal end of the connector 301 such that any movement of the base 302 relative to the connector 301 is minimized or prevented. For example, the base 302 may be mounted or otherwise attached to the distal end of the connector 301 via a first plurality of screws (obscured from the view in FIG. 3) and/or any other similar connecting mechanisms. However, in some implementations, the base 302 and the connector 301 may be manufactured seamlessly in order to constitute a unique or unitary/integral part. The base 302 may further include a plurality of restraining cylinders 307 (one of the restraining cylinders is obscured from the view in FIG. 3). In some implementations, the ring-type member 304 may be disposed rotationally and slidably between the restraining cylinders 307. For purposes of this disclosure, a component or portion of a device that is disposed rotationally is capable of rotational motion. In addition, a component is connected movably to something when it is secured in a manner that still allows and facilitates movement of the component. In some implementations, the restraining cylinders 307 may be configured to prevent linear movements of the ring member 304 in all translational directions. Furthermore, in one implementation, the restraining cylinders 307 may only allow for rotational movement of the ring-type member 304 in the direction of the first rotational degree of freedom 207.

In different implementations, the first frictional gripper 303 may be mounted or otherwise attached to the base 302 such that the first frictional gripper acts as, for example, a cantilever beam. In one implementation, the first frictional gripper 303 may be mounted or otherwise attached to the base 302 by a second plurality of screws 308 and/or any other similar connecting mechanisms. However, in some implementations, the base 302 and the first frictional gripper 303 may be manufactured seamlessly in order to constitute a unique or unitary/integral part. Furthermore, in one implementation, a first lock screw 309 may be secured at a distal end of the first frictional gripper 303 to provide a locking mechanism for the ring-type member 304. In order to promote a friction between the first frictional gripper 303 and the ring-type member 304, the distal end of the first frictional gripper 303 may be bent via tightening of the first lock screw 309. The friction between the first frictional gripper 303 and the ring-type member 304 may provide a locking mechanism against external forces/torques urging movement relative to the first rotational degree of freedom 207. The friction between the first frictional gripper 303 and the ring-type member 304 thereby minimizes or prevents the rotational movement of the ring-type member 304 in the direction of the first rotational degree of freedom 207. More specifically, the friction between the first frictional gripper 303 and the ring-type member 304 prevents externally-urged rotational movement of the surgical fine-tuning device 200 in the direction of the first rotational degree of freedom 207. The surgeon can also loosen the first lock screw 309 to allow for movement of the ring-type member 304 in the direction of the first rotational degree of freedom 207 and thereby allow an alteration in the position of the surgical device in the direction of the first rotational degree of freedom 207. Similarly, the surgeon can also tighten the lock screw 309 to prevent the externally-urged rotational movement of the ring-type member 304 in the direction of the first rotational degree of freedom 207, thereby locking movement of the surgical fine-tuning device 200 in the direction of the first rotational degree of freedom 207. In some implementations, the ring-type member 304 may be graded on an upper surface thereof to allow the surgeon to measure the surgical fine-tuning device 200 disposition in the direction of the first rotational degree of freedom 207.

Figure 4:
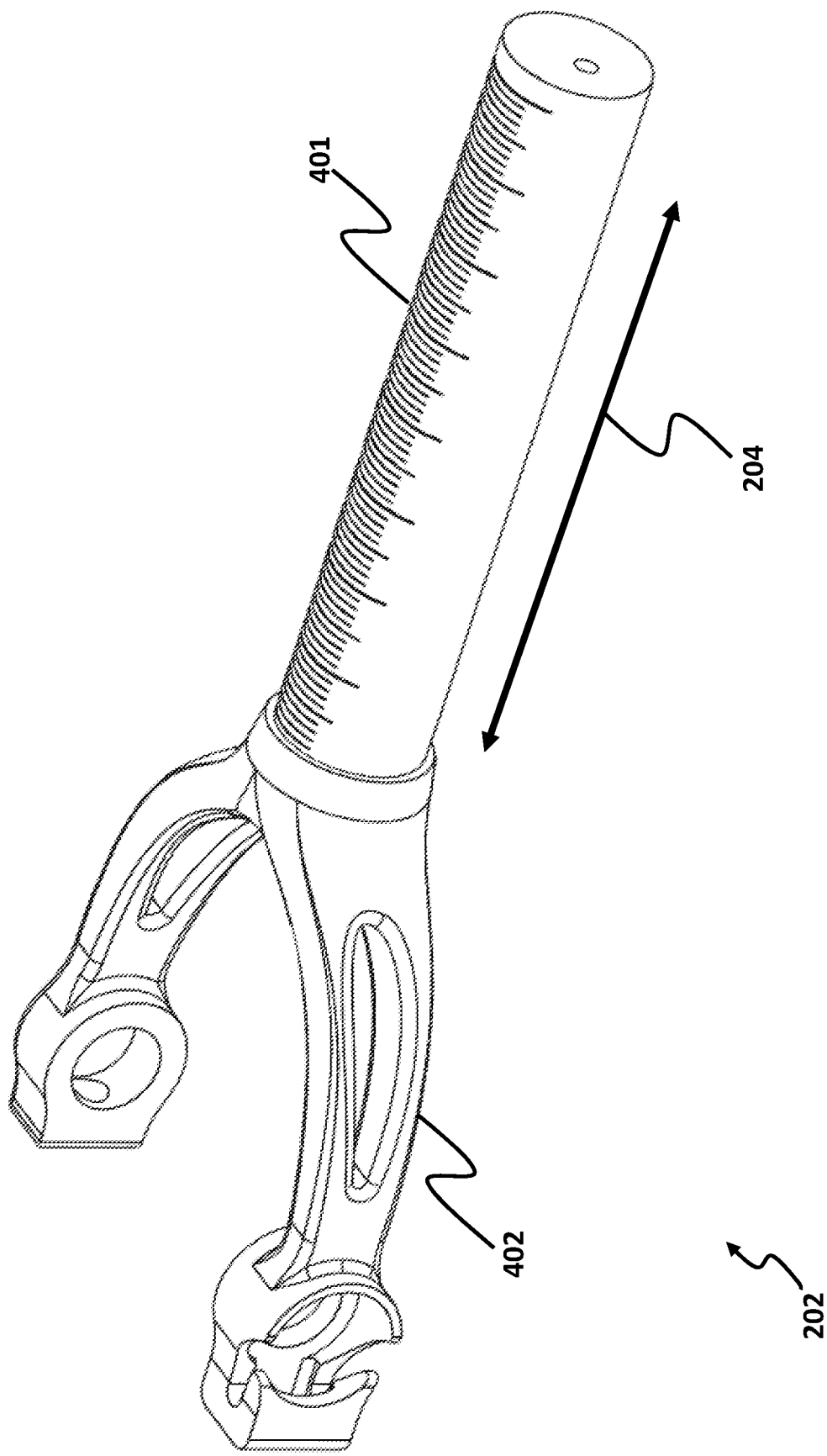
FIG. 4 illustrates a detailed perspective view of an implementation of a translational mechanism of a surgical device, which can be associated with various surgical apparatuses.

For purpose of reference, FIG. 4 provides an overview of various components and features of one implementation of the surgical fine-tuning device 200 that is configured to provide the translational degree of freedom 204. FIG. 4 illustrates a perspective view of the translational mechanism 202. The translational mechanism 202 may include a main rod 401, and a C-type connector 402. The main rod 401 may be connected to the C-type connector 402 such that any movement of the main rod 401 relative to the C-type connector 401 is minimized or prevented. For example, the main rod 401 may be fitted tightly from a distal end thereof in a proximal end of the C-type connector 402 through a press fit process or via any other connection mechanisms. However, in some implementations, the main rod 401 and the C-type connector 402 may be manufactured seamlessly in order to constitute a unique or unitary/integral part. With reference to FIGS. 2-4, in one implementation, the main rod 401 may be disposed slidably from a proximal end thereof in a pipe section 310 of the ring-type member 304 to provide the translational degree of freedom 204 to the surgical fine-tuning device 200. In order to prevent the main rod 401 from leaving the pipe section 310, a cap 212 may be laid on the proximal end of the main rod 401. In some implementations, in order to provide a locking facility in the direction of the translational degree of freedom 204, a second frictional gripper 311 may be provided at the distal end of the pipe section 310. The second frictional gripper 311 may be provided by cutting approximately a half part of the distal end of the pipe section 310. In some other implementation, the second frictional gripper 311 may be provided at the distal end of the pipe section 310 by, for example, attaching a bendable part to the distal end of the pipe section 310 or any other mechanisms. The second frictional gripper 311 may act as, for example, a cantilever, and therefore by pushing a force at the free end of the second frictional gripper 311 a friction force may be promoted against movement of the translational mechanism 202. In some implementations, in order to push a force at the free end of the second frictional gripper 311, a second lock screw 312 may be utilized. The surgeon can loosen the second lock screw 312 to allow for movement of the translational mechanism 202 in the direction of the translational degree of freedom 204 and thereby allow for altering the surgical device position in the direction of the translational degree of freedom 204. The surgeon can also tighten the second lock screw 312 to prevent the translational movement of the ring-type member 304 in a direction of the translational degree of freedom 207 and thereby lock movement of the surgical fine-tuning device 200 in the direction of the translational degree of freedom 204. In some implementations, the main rod 401 may be graded on an outer surface thereof to allow the surgeon to measure the disposition of the surgical fine-tuning device 200 in a direction of the translational degree of freedom 204.

Figure 5:
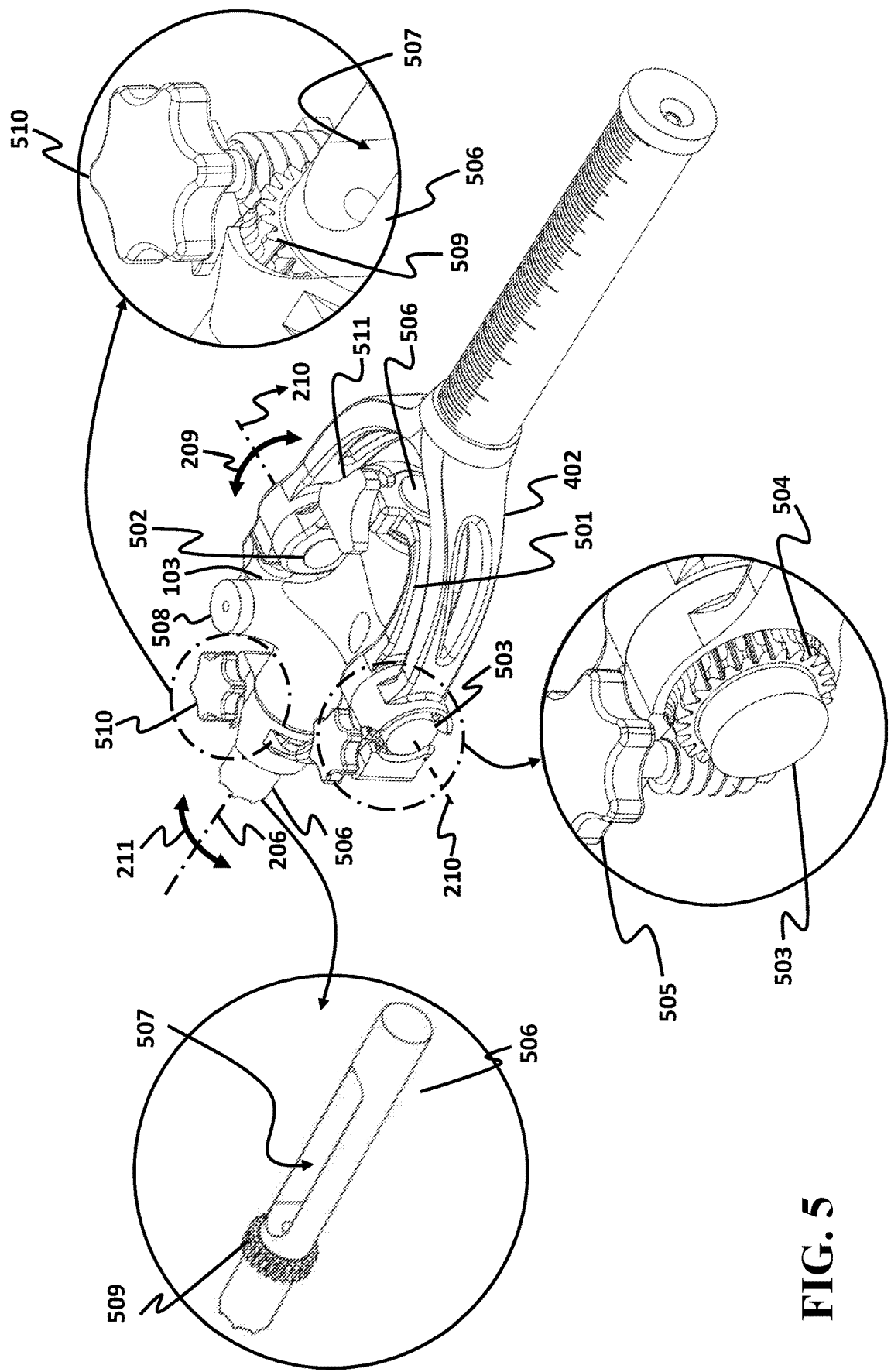
FIG. 5 illustrates a detailed perspective view of an implementation of second rotational mechanism of a surgical device, which can be associated with various surgical apparatuses.

FIG. 5 illustrates, graphically, an overview of various components and features of an implementation of the surgical fine-tuning device 200 respectively configured to operate together to provide the second rotational degree of freedom 209 and the third rotational degree of freedom 211. As shown in FIG. 5, in one implementation, a circular frame 501 may be disposed coaxially rotatable in the C-type connector 402 (the common axis is the pitch axis 210). In some implementations, a first connecting rod 502 and a second connecting rod 503 may be used to associate the circular frame 501 to the C-type connector 402. In one implementation, the first connecting rod 502 and the second connecting rod 503 may be fitted tightly to lateral holes (not labeled in FIG. 5) of the circular frame 501. In addition, the first connecting rod 502 and the second connecting rod 503 may be disposed freely in lateral holes (not labeled in FIG. 5) of the C-type connector 402 in some cases. In other words, an association between the circular frame 501 and the C-type connector 402 may be provided such that the circular frame 401 and the first connecting rod 502 and the second connecting rod 503 can rotate substantially or entirely synchronously about the pitch axis 210 with minimal or zero surplus rotation of the C-type connector 402 about the pitch axis 210. In some implementations, a first worm gear 504 may be provided on an outer surface of the second connecting rod 503. The first worm gear 504 can have a meshed engagement with a first worm screw 505. It can be understood that responsive to rotational movement of the first worm screw 505, the end-effector 103 may rotate with a relatively small resolution (due to the gear ratio between the first worm gear 504 and the first worm screw 505) about the pitch axis 210. The meshed engagement between the first worm gear 504 and the first worm screw 505 can allow a surgeon to accurately alter the end-effector 103 position in the direction of the second rotational degree of freedom 209. For example, in some implementations, the surgeon can rotate the end-effector 103, as much as approximately 0.5°, about the pitch axis 210 by rotating the first worm screw 505. It will be understood that meshed engagement between the first worm gear 504 and the first worm screw 505 can provide a self-locking mechanism against external forces/torques urging movement of the end-effector 103 relative to the second rotational degree of freedom 209. Utilization of the first worm gear 504 and the first worm screw 505 for altering the end-effector 103 position in the direction of the second rotational degree of freedom 209 can provide significant benefits, including but not limited to an increase in positioning precision through preventing end-effector 103 dispositions or displacements that might otherwise be caused by a locking procedure (for example, tightening a lock screw). However, in some implementations, in order to ensure the end-effector locking against external forces/torques urging movement of the end-effector 103 relative to the second rotational degree of freedom 209, an additional locking mechanism over the self-locking mechanism may be used. For example, in one implementation, a third lock screw (obscured from view in FIG. 5) may be attached to one lateral side of the C-type connector 402. Tightening the third lock screw may promote, induce, or be otherwise associated with increased friction between the third lock screw and the first connecting rod 502 that minimizes or prevents any movement of the end-effector 103 in direction of the second rotational degree of freedom 209. Once the positioning of the end-effector 103 is accomplished, the surgeon can tighten the third lock screw to ensure the end-effector 103 locking in the direction of the second rotational degree of freedom 209.

Referring back to FIG. 5, in some implementations, a slotted rod 506 may be disposed freely in the bottom and top holes (not labeled in FIG. 5) of the circular frame 501, such that the slotted rod 506 is able to rotate freely along the bottom and a top holes (not labeled in FIG. 5) of the circular frame 501. In one implementation of the present disclosure, the slotted rod 506 may be fitted tightly or snugly in the end-effector 103 such that end-effector 103 rotates substantially synchronously with the slotted rod 506 in response to rotation of the slotted rod 506 in the direction of the third rotational degree of freedom 211. In some implementations, a slot 507 may be provided on the slotted rod 506. The slot 507 may allow for a biopsy needle guide 508 to be disposed in a passage of the end-effector 103 to guide the biopsy needle to the target.

In addition, in different implementations, a second worm gear 509 may be provided on an outer surface of the slotted rod 506. The second worm gear 509 can have a meshed engagement with a second worm screw 510. It can be understood that responsive to rotational movement of the second worm screw 510, the end-effector 103 may rotate with a relatively small resolution (due to the gear ratio between the second worm gear 509 and the second worm screw 510) about the roll axis 206. The meshed engagement between the second worm gear 509 and the second worm screw 510 can allow a surgeon to accurately position the end-effector 103 in the direction of the third rotational degree of freedom 211. For example, the surgeon can rotate the end-effector 103, as much as approximately 0.5° about the roll axis 206 by rotating the second worm screw 510. It should be understood that meshed engagement between the second worm gear 509 and the second worm screw 510 can offer a self-locking mechanism against external forces/torques urging movement of the end-effector 103 relative to the third rotational degree of freedom 211. Utilization of the second worm gear 509 and the second worm screw 510 for altering the end-effector 103 position in the direction of the third rotational degree of freedom 209 can provide significant benefits, including but not limited to an increase in positioning precision through prevention of end-effector 103 dispositions or displacements caused by a locking procedure (for example, tightening a lock screw). However, in some implementations, in order to more strongly ensure the end-effector locking against external forces/torques urging movement of the end-effector 103 relative to the third rotational degree of freedom 209, an additional locking mechanism over the self-locking mechanism may be used. For example, in one implementation, a fourth lock screw 511 may be attached to a top side of the C-type connector 402. Tightening the fourth lock screw 511 may promote, induce, or otherwise be associated with increased friction between the fourth lock screw 511 and the slotted rod 506 that minimizes or prevents any externally-urged movement of the end-effector 103 in the direction of the third rotational degree of freedom 209. Once the positioning of the end-effector is accomplished, the surgeon can tighten the fourth lock screw to ensure the end-effector 103 locking in the direction of the third rotational degree of freedom 209.

As presented herein, the disclosed system and device can allow a surgeon to accurately identify a path for a biopsy needle by means of a minimally invasive procedure. The DOFs of the disclosed robotic guide allow the surgeon to position and secure the end-effector thereof to the target with high accuracy. The surgeon may provide a manual coarse positioning/securing for the surgical device through the passive DOFs of the coarse-tuning section before implementation of the fine positioning/securing through other DOFs of the fine-tuning section. The coarse positioning/securing through the coarse-tuning section can help place the surgical device in a position near to the target, thereby facilitating the surgeon's ability to secure the end-effector exactly to the target, despite its limited range of operation. For purpose of reference, it can be understood upon reading this disclosure that some implementations of the surgical apparatus 100, for reasons including a desire for compactness, may have certain limits on ranges of one or more of the DOFs. For example, referring back to FIG. 2, the first rotational degree of freedom 207 may be configured to allow the first rotational mechanism 201 about the roll axis 105 within a range, for example, between approximately −60° and approximately +60°. Similarly, translational motion of the translational mechanism 202 along the translational degree of freedom 204, can be limited to another range, for example, between 0 mm and approximately +40 mm. In one or more implementations, the second rotational degree of freedom 210 may be configured to allow rotational motion of the end-effector 103 about the pitch axis 210 within a range, for example, between approximately −20° and approximately +20°. Furthermore, in some implementations, the third rotational degree of freedom 211 may be configured to allow rotational motion of the end-effector 103 about the roll axis 206 within a range, for example, between approximately −30° and approximately +30°. It will be understood that the above examples of limits of the first rotational degree of freedom about the yaw axis 208, the second rotational degree of freedom about the pitch axis 210, the third rotational degree of freedom about the roll axis 206, and the translational degree of freedom along the roll axis 206 are for purposes of example only, and are not intended as any limitation of ranges of the surgical device DOFs in implementations according to aspects of this disclosure.

Thus, the disclosed system and method provide a surgeon significantly improved precision during procedures, facilitating the positioning of a device in conjunction with 3D imaging and surgical navigation technology. This device provides freedom from the bulk and assembly of a frame in a biopsy surgery while increasing the capacity of the system to be adjusted along multiple degrees of freedom. The disclosed device is equipped to provide a substantially exact positioning mechanism and biopsy needle diameter adapter. Furthermore, the invasive attachment to a skull is no longer required.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study, except where specific meanings have otherwise been set forth herein. Relational terms such as "first" and "second" and the like may be used solely to distinguish one entity or action from another without necessarily requiring or implying any actual such relationship or order between such entities or actions. The terms "comprises," "comprising," or any other variation thereof, as used herein and in the appended claims are intended to cover a non-exclusive inclusion, encompassing a process, method, article, or apparatus that comprises a list of elements that does not include only those elements but may include other elements not expressly listed to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is not intended to be used to interpret or limit the scope or meaning of the claims. In addition, in the foregoing Detailed Description, it can be seen that various features are grouped together in various implementations. Such grouping is for purposes of streamlining this disclosure and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into this Detailed Description, with each claim standing on its own as a separately claimed subject matter.

While various implementations have been described, the description is intended to be exemplary, rather than limiting and it will be apparent to those of ordinary skill in the art that many more implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in the light of the attached claims and their equivalents. Also, various modifications and changes may be made within the scope of the attached claims.

What is claimed is:

1. A surgical device for guiding a biopsy surgical tool, the surgical device comprising:
   a first rotational mechanism configured to provide a first rotational degree of freedom about a yaw axis to the surgical device, the first rotational mechanism including:
   a connector connected movably to a distal end of a coarse-tuning section in a configuration rotatable about a roll axis, the yaw axis, and a pitch axis,
   a base, fixedly attached to a distal end of the connector,
   a ring-type member movably connected to a distal end of the base in a configuration rotatable about the yaw axis,
   a plurality of restraining cylinders attached to the distal end of the base, the ring-type member disposed rotationally and slidably between the plurality of restraining cylinders in a configuration limiting motion of the ring-type member to a rotation about the yaw axis,
   a pipe-shaped section provided at a distal end of the ring-type member, and
   a first frictional gripper attached to the base with a first lock screw mounted on the first frictional gripper, the first frictional gripper configured to minimize movements of the ring-type member in response to the first lock screw being tightened on the first frictional gripper;
   a translational mechanism configured to provide a translational degree of freedom along the roll axis to the surgical device, the translational mechanism including:
   a main rod disposed slidably, from a proximal end thereof, along a distal end of the pipe-shaped section of the ring-type member in a configuration limiting the movements of the main rod to a translational movement along the roll axis,
   a c-type connector fitted securely, from a proximal end thereof, to a distal end of the main rod,
   a second frictional gripper provided at the distal end of the main rod and a second lock screw mounted on the second frictional gripper, the second frictional gripper configured to minimize movements of the main rod in response to the second lock screw being tightened on the second frictional gripper; and
   a second rotational mechanism configured to provide both a second rotational degree of freedom about the pitch axis and a third rotational degree of freedom about the roll axis to the surgical device, the second rotational mechanism including:
   a circular frame disposed coaxially and movably inside the c-type connector in a configuration rotatable about the pitch axis,
   a slotted rod disposed movably inside the circular frame in a configuration rotatable about the roll axis,
   an end-effector mounted securely on the slotted rod in a configuration synchronously rotatable with the slotted rod about the roll axis,
   a first worm gear attached to the circular frame and a first worm screw attached to the c-type member, the first worm gear meshing with the first worm screw in a configuration that is responsive to the first worm screw being turned in either a clockwise direction or a counterclockwise direction, the circular frame thereby rotating about the pitch axis, and
   a third lock screw, mounted on the c-type member in a configuration wherein tightening the third lock screw promotes friction between the third lock screw and the circular frame, thereby minimizing movements of the circular frame.

2. A surgical device for guiding a biopsy surgical tool, the surgical device comprising:
   a first rotational mechanism configured to provide a first rotational degree of freedom about a yaw axis to the surgical device, the first rotational mechanism including:
   a connector connected movably to a distal end of a coarse-tuning section in a configuration rotatable about a roll axis, the yaw axis, and a pitch axis,
   a base, fixedly attached to a distal end of the connector, and a ring-type member movably connected to a distal end of the base in a configuration rotatable about the yaw axis, the surgical device further comprising:

a second rotational mechanism configured to provide both a second rotational degree of freedom about the pitch axis and a third rotational degree of freedom about the roll axis to the surgical device, the second rotational mechanism including:

a circular frame disposed coaxially and movably inside a c-type connector in a configuration rotatable about the pitch axis, a slotted rod disposed movably inside the circular frame in a configuration rotatable about the roll axis, and an end-effector mounted securely on the slotted rod in a configuration synchronously rotatable with the slotted rod about the roll axis, the surgical device further comprising:

a first worm gear attached to the circular frame and a first worm screw attached to the c-type member, the first worm gear meshing with the first worm screw in a configuration that is responsive to the first worm screw being turned in either a clockwise direction or a counterclockwise direction, the circular frame thereby rotating about the pitch axis, a second worm gear attached to the slotted rod and a second worm screw attached to the circular frame, the second worm gear meshing with the second worm screw in a configuration that is responsive to the second worm screw being turned in either a clockwise direction or a counterclockwise direction, the end-effector thereby rotating about the roll axis.

3. The surgical device of claim 2, further comprising a plurality of restraining cylinders attached to the distal end of the base, the ring-type member disposed rotationally and slidably between the plurality of restraining cylinders in a configuration limiting motion of the ring-type member to a rotation about the yaw axis.

4. The surgical device of claim 2, further comprising a pipe-shaped section provided at a distal end of the ring-type member.

5. The surgical device of claim 2, further comprising a first frictional gripper attached to the base with a first lock screw mounted on the first frictional gripper, the first frictional gripper configured to minimize movements of the ring-type member in response to the first lock screw being tightened on the first frictional gripper.

6. The surgical device of claim 5, further comprising:

a translational mechanism configured to provide a translational degree of freedom along the roll axis to the surgical device, the translational mechanism including:

a main rod disposed slidably, from a proximal end thereof, along a distal end of the pipe-shaped section of the ring-type member in a configuration such that the movement of the main rod is limited to a translational movement along the roll axis, and the c-type connector fitted securely, from a proximal end thereof, to a distal end of the main rod.

7. The surgical device of claim 6, further comprising a second frictional gripper provided at the distal end of the main rod and a second lock screw mounted on the second frictional gripper, the second frictional gripper configured to minimize movements of the main rod in response to the second lock screw being tightened on the second frictional gripper.

8. The surgical device of claim 7, further comprising a third lock screw mounted on the circular frame in a configuration wherein tightening the third lock screw promotes friction between the third lock screw and the slotted rod, thereby minimizing movements of the slotted rod.

9. The surgical device of claim 8, further comprising a fourth lock screw mounted on the c-type member in a configuration wherein tightening the fourth lock screw promotes friction between the fourth lock screw and the circular frame, thereby minimizing movements of the circular frame.

10. The surgical device of claim 6, wherein the main rod is graded on an outer surface thereof, thereby facilitating measurement of the surgical fine-tuning device disposition in the direction of the translational degree of freedom.

11. The surgical device of claim 2, wherein the ring-type member is graded on an upper surface thereof, thereby facilitating measurement of the surgical fine-tuning device disposition in the direction of the first rotational degree of freedom.

\* \* \* \* \*